United States Patent [19]

Mixich et al.

[11] Patent Number: 4,550,175
[45] Date of Patent: *Oct. 29, 1985

[54] PROCESS FOR THE STEREOSPECIFIC PREPARATION OF (Z)-1-(2,4-DICHLOROPHENYL)-2-(IMIDAZOL-1-YL)-0-(2,4-DICHLOROBENZYL)-ETHANONE OXIME ETHER

[75] Inventors: Georg Mixich; Kurt Thiele, both of Zofingen, Switzerland

[73] Assignee: Siegfried Aktiengesellschaft, Zofingen, Switzerland

[21] Appl. No.: 589,938

[22] Filed: Mar. 15, 1984

[*] Notice: The portion of the term of this patent subsequent to Apr. 17, 2001, has been disclaimed.

Related U.S. Application Data

[63] Continuation-in-part of Ser. No. 412,943, Aug. 30, 1982, Pat. No. 4,443,612, which is a continuation of Ser. No. 211,172, Nov. 28, 1980, abandoned, which is a continuation-in-part of Ser. No. 40,425, May 18, 1979, abandoned.

[30] Foreign Application Priority Data

May 24, 1978 [CH] Switzerland .......... 5653/78
Jan. 9, 1979 [CH] Switzerland .......... 161/79

[51] Int. Cl.⁴ .......................... C07D 233/61
[52] U.S. Cl. .......................... 548/341
[58] Field of Search .......................... 548/341

[56] References Cited

U.S. PATENT DOCUMENTS

| | | | |
|---|---|---|---|
| 2,880,238 | 3/1959 | Kundiger et al. | 564/256 |
| 3,236,889 | 2/1966 | Pawloski | 564/256 |
| 3,441,608 | 4/1969 | Schutz et al. | 564/257 |
| 3,903,164 | 9/1975 | Goransson-Dahlander | 564/257 |
| 4,038,317 | 7/1977 | Wermuth et al. | 564/256 |
| 4,124,767 | 11/1978 | Mixich et al. | 548/341 X |

Primary Examiner—Richard A. Schwartz
Attorney, Agent, or Firm—Burns, Doane, Swecker & Mathis

[57] ABSTRACT

For preparing substantially pure (Z)-1-(2,4-dichlorophenyl)-2-(imidazol-1-yl)-0-(2,4-dichlorobenzyl)-ethanone oxime ether having the formula

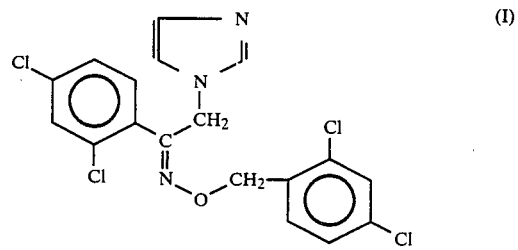

i.e. the cis-isomer of said oxime ether in a stereospecifically pure form, the pure (Z)-stereoisomer of the corresponding ethanone oxime is first converted into an alkali salt in a polar solvent, such as acetone or dimethylformamide, using an alkali in an amount somewhat less than the equimolar amount with respect to the said ethanone oxime, and is then converted to the desired ether by reacting it at a temperature not higher than 40° C. with a halogen compound capable of forming the desired ether. Isolation of the ether product is obtained as the free base or by precipitating it as an acid addition salt upon addition of a suitable organic or mineral acid, preferably nitric acid.

3 Claims, No Drawings

PROCESS FOR THE STEREOSPECIFIC PREPARATION OF (Z)-1-(2,4-DICHLOROPHENYL)-2-(IMIDAZOL-1-YL)-0-(2,4-DICHLOROBENZYL)-ETHANONE OXIME ETHER

CROSS-REFERENCE TO EARLIER APPLICATIONS

This application is a continuation-in-part of U.S. application Ser. No. 412,943 filed Aug. 30, 1982, now U.S. Pat. No. 4,443,612, which is a continuation application of Ser. No. 211,172 filed Nov. 28, 1980, now abandoned, which in turn is a continuation-in-part of Ser. No. 040,425 filed May 18, 1979, now abandoned.

The files of the said parent application Ser. No. 040,425 contain the original priority documents corresponding to the two Swiss applications 5653/78 filed May 24, 1978 and 161/79 filed Jan. 9, 1979, the benefit of which is hereby claimed anew for this continuation application.

SUMMARY OF THE INVENTION

The invention concerns a process for the stereospecific preparation of substantially pure (Z)-1-(2,4-dichlorophenyl)-2-(imidazol-1-yl)-O-(2,4-dichlorobenzyl)-ethanone oxime ether, i.e. the cis-isomer form, synonymously called (Z)-isomer form, having the formula

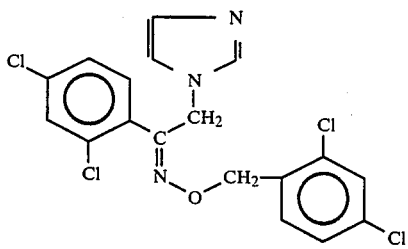

or an acid addition salt thereof with a teleologically acceptable acid; which comprises
(1) suspending substantially pure (Z)-1-(2,4-dichlorophenyl)-2-(imidazol-1-yl)-ethanone oxime in about five times its weight of acetone,
(2) adding to the resulting suspension solid KOH in finely subdivided form with vigorous agitation in an amount that is about 5 to 15 mole % less than the equimolar amount of KOH relative to said oxime, and continuing the agitation until the oxime is dissolved,
(3) adding to the resulting solution an approximately equimolar amount of 2,4-dichlorobenzyl chloride and thereafter stirring the reaction mixture while maintaining it at a temperature not in excess of 40° C. until substantially complete reaction has been obtained, and
(4) pouring the reaction mixture into water or an aqueous solution of a teleologically acceptable acid and recovering the (Z)-oxime ether product therefrom.

The invention also concerns an above process, wherein aqueous nitric acid is added to the aqueous reaction mixture in step (4), whereby the (Z)-oxime ether is precipitated as a nitrate salt, and wherein the (Z)-oxime ether product is recovered in the form of its nitrate.

PRIOR ART

Imidazolyloxime compounds of the formula (II) and imidazolyl oxime ether derivatives prepared from them are disclosed in U.S. Pat. No. 4,124,767. This reference also specifically discloses that one of the two possible stereoisomeric oximes is formed when 2,4-dichlorophenacyl imidazole is oximated in the laboratory with hydroxylammonium chloride in ethanol in the presence of pyridine, whereas in the absence of pyridine the other one of the two stereoisomeric oximes is formed under otherwise identical conditions. Relatively pure 1-(2,4-dichlorophenyl)-2-(imidazol-1-yl)-ethanone oximes were thus obtained. A stereochemical identification of the compounds was not accomplished.

However, further work along these lines has surprisingly shown that the specific reactions previously disclosed are not sufficiently reproducible when scaled up to a commercial scale and, moreover, are not applicable to the conversion of analgous compounds. In attempting to carry out such a stereospecific synthesis on a commercial scale, or to apply it to analogous reactions, isomeric mixtures rather than the pure isomers were obtained. Further tests did show that this also is true when carrying out the known process in the laboratory scale, regardless of the presence or absence of pyridine. Upon recrystallization of the isomeric mixtures the less soluble cis-oxime in fact is obtainable therefrom, but the yield is poor.

The 1-(2,4-dichlorophenyl)-2-(imidazol-1-yl)-ethanone oximes described in U.S. Pat. No. 4,124,767 were also disclosed there to have been etherified in dimethylformamide in the presence of an equimolar amount of sodium hydride, based on the oxime, at a temperature gradually increasing from room temperature to 80° C. In this etherification the stereoisomers of 1-(2,4-dichlorophenyl)-2-(imidazol-1-yl)-ethanone oxime-(2,4-dichlorobenzyl) ether are likewise alleged to have been obtained, again, however, without stereochemical identification.

Subsequent work along these lines has likewise shown that the etherification disclosed in the prior art definitely does not proceed stereospecifically, when it is scaled up to a commercial scale. The NMR spectral and TLC plates clearly show that under commercial-scale conditions also substantial amounts of the other unwanted stereoisomer, namely the (E)-isomer, are obtained in the commercial product, although a sterically pure isomer can be obtained after separation and purification when working on a small scale. The reproducibility, productivity and the yield (21%) of said known process are poor.

Thus, of course, it is desirable to produce the (Z)-oxime ether compound in a stereochemically pure form on a large scale, because of its significant antimycotic activity. While preparation of such pure isomers is achievable in the laboratory, for instance by chromatographic separation, such chromatographic and equivalent separations are not economical and not feasible on a commercial scale.

OBJECTS OF THE INVENTION

It is therefore an object of this invention to provide a commercially practical process for the stereospecific preparation of the (Z)-imidazolyl oxime ether having the formula

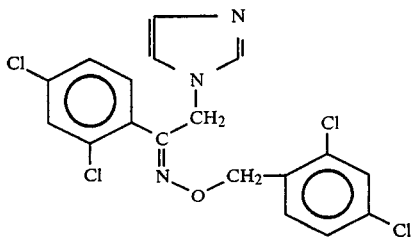

(I)

or an acid addition salt thereof with a teleologically acceptable acid.

More particularly, it is an object to provide such a process that is capable of yielding the desired pure stereoisomer in a dependable and reproducible manner and in acceptable yields regardless of the scale of operation.

GENERAL DESCRIPTION

According to this invention such production is achieved by suspending or dissolving substantially pure (Z)-1-(2,4-dichlorophenyl)-2-(imidazol-1-yl)-ethanone oxime having the formula

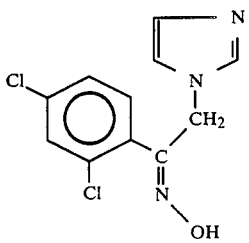

(II)

in about five times its weight of acetone, adding to the resulting suspension solid KOH in finely subdivided form with vigorous agitation in an amount that is about 5 to 15 mole % less than the equimolar amount of KOH relative to said oxime, and continuing the agitation until the oxime is dissolved, adding to the resulting solution an approximately equimolar amount of 2,4-dichlorobenzyl chloride and thereafter stirring the reaction mixture while maintaining it at a temperature not in excess of 40° C. until substantially complete reaction has been obtained, and pouring the reaction mixture into water or an aqueous solution of a teleologically acceptable acid and recovering the oxime ether product therefrom. A preferred method for recovering said ether is a process, wherein aqueous nitric acid is added to the aqueous reaction mixture in the recovering step, whereby the oxime ether is precipitated as a nitrate salt, and wherein the oxime ether product is recovered in the form of its nitrate.

In the above step of forming the metal oximate of the cis-oxime it is one of the most important features of the invention that the basic metal compound used for forming the metal oximate shall be present in the reaction system only in an amount which is somewhat less, preferably about 5 to 15 mole % less than the equimolar amount of said metal compound relative to said oxime-isomer of formula (II). If the metal compound is present in an amount equal to or greater than said equimolar amount, then an isomerization will occur and the obtainable product is but a mixture of the two stereoisomeric ethers, namely of the (Z)-oxime ether and the (E)-oxime ether rather than a stereochemically pure compound, i.e. the desired cis- or (Z)-configuration.

For achieving the objects of the invention it is a further essential feature of the invention that the oxime compound of formula (II) is provided as a pure substance in its stereoisomeric (Z)-form when carrying out the above etherification reaction. For producing said stereoisomer one starts with the corresponding 2-halogen ethanone of the formula

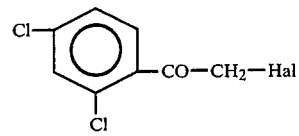

(III)

wherein Hal is a halogen atom, e.g., chlorine, bromine, iodine or fluorine. In preparing the cis-oxime (II) the ethanone (III) is first reacted with imidazole or an imidazole compound having the desired substituents so as to produce the corresponding 2-(imidazol-1-yl) compound and the latter is subsequently heated in methanol, ethanol or similar alcoholic solution in the presence of a molar excess of an alkali with hydroxylamine or a hydroxylamine compound that liberates hydroxylamine under the reaction conditions, thereby producing the desired cis-oxime product (II). As free hydroxylamine is relatively unstable, it is generally preferable to use acid salts thereof such as hydroxylammonium sulfate, sodium hydroxylamine mono- or disulfonate or the like as a source for the required hydroxylamine. It is a further important feature of the invention that the above cis-oximation is carried out in the presence of an alkali in an amount corresponding to a substantial molar excess, preferably to at least double the equimolar amount, for example from about two times to about eight times the equimolar amount, relative to said hydroxylamine and hydroxylamine-yielding compound, respectively. This condition shall include as a matter of fact the understanding that the amount of the alkali simultaneously shall correspond to a molar excess relative to said 2-(imidazol-1-yl)-ethan-1-on derivative. When carrying out the oximation of the imidazolyl substituted ethanone derivative in the absence of said molar excess of an alkali, isomerization will take place and a mixture of the corresponding cis and trans oximes is obtained instead of a stereochemically pure cis-oxime.

In the single known case mentioned earlier herein of a reported preparation of the stereoisomeric imidazolyl oxime ether compound of formula (I) the etherification that was reportedly essentially stereospecific when conducted on a small scale has thus far not been successfully translated into a commercial-scale process in a sufficiently reproducible manner, nor has it been found practical for the preparation of other, analogous compounds, nor has it been found to be even safely reproducible on a laboratory scale. The reason for such failure, as now has been revealed, is in the known process the use of an equimolar amount of alkali rather than a sub-equimolar amount. It has been found that suprisingly the presence of an alkali in an amount of equal to or greater than the equimolar amount relative to said oxime compound has a catalytic effect on the isomerization reaction. However, isomerization during the etherification can be completely excluded in the presence of a sub-equimolar amount of an alkali. The invention thus provides a secure, reproducible, practical, commercial-scale process for the stereoselective and stereospecific preparation of the (Z)-1-(2,4-dichlorophenyl)-2-(imidazol-1-yl)-O-(2,4-dichlorobenzyl)-ethanone oximer ether, i.e., the oxime ether in its cis-isomer form.

The same is also true with respect to the stereospecific and stereoselective preparation of the imidazolyl ethanone oxime compound (II), which is required as an intermediate in the preparation of the oxime ether. More particularly, when preparing the cis-oxime (II) according to this invention, the corresponding 2-halogen ethanone (III) is first imidazolated and only then oximated in the presence of a molar excess of an alkali.

The stereoisomeric (E)- and (Z)-imidazolyl oxime ether compounds exhibit different melting points, a distinctly different chromatographic behaviour, likewise particularly RF values that are clearly different in a thin-layer chromatogram (TLC). The products can clearly be identified from the NMR spectrum as the cis form or trans form, i.e., the (E)-form or the (Z)-form. This identification of a product as one or the other isomer is also particularly possible because of the displacement of the CH$_2$ protons ($\delta_{cis} > \delta_{trans}$).

According to a further development of this invention the stereospecific etherification for the preparation of the cis-isomer (I) is preferably carried out in a lower ketone solvent such as acetone in combination with an alkali metal hydroxide, e.g., KOH or NaOH, the quantity of hydroxide added being somewhat smaller than equimolar, preferably about 5 to 15 mol percent smaller than the equimolar amount of hydroxide relative to the oxime. The imidazolyl oxime ether compound so prepared is preferably isolated from the reaction mixture as an acid addition salt upon addition of a suitable organic or mineral acid, e.g., aqueous hydrochloric, sulfuric, phosphoric, nitric, acetic, citric, tartaric, malonic, maleic, fumaric, succinic, salicyclic, lactic, glycolic, benzoic, para-aminobenzoic, methanesulphonic or cyclohexylsulfaminic acid. Aqueous nitric acid is generally preferred, although any other salt forming acid that is teleologically acceptable, i.e., acceptable for the particular intended end use of the product, e.g., as a fungicide or bactericide, can be used similarly. Obviously, for instance, when the product is to be applied as a fungicide or bactericide to an animal or to an agricultural crop which is to be rid of a fungus or bacteria, the selected acid should be one that is not unduly injurious to the animal or the crop.

The stereoisomerically pure (Z)-imidazolyl ethanone oxime compound required as an intermediate is prepared as described above. In any case, the recovery of the respective individual (Z)-stereoisomer in a form substantially free from its (E)-stereoisomer is desirable not only when it is used as an intermediate in the synthesis of more complex stereoisomeric derivatives thereof, but also when it is used as a biological agent having biocidal properties that are specifically different from those of its other stereoisomer.

The greatest value of the invention is currently believed to reside in the fact that the compounds corresponding to formulae I or II can be conveniently prepared in a stereochemically pure form on a commercial scale.

SPECIFIC EMBODIMENTS

The invention is further illustrated by the following working example.

EXAMPLE (a) Preparation of (Z)-1-(2,4-dichlorophenyl)-2-(imidazol-1-yl)-ethanone oxime

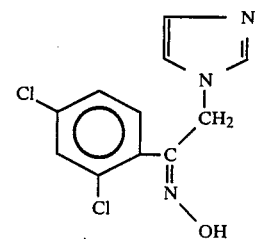

1205 g (5.4 moles) 2,4-dichlorophenacyl chloride is dissolved in 1800 ml dichloromethane and the solution is then added dropwise within a time of about 6 hours to a suspension of 1101 g (16.2 moles) imidazole in 5500 ml dichloromethane while vigorously stirring and maintaining the temperature of the reaction mixture at about 0° C. to 5° C. Thereafter the mixture is continually stirred at this temperature for 1 hour. Stirring then is continued for about 16 hours at room temperature. The solvent then is distilled off in a vacuum evaporator keeping the temperature of the reaction mixture below 40° C. The residue is poured into 6 l. water, and the obtained mixture is vigorously stirred, whereupon the reaction product is precipitated. The reaction product is filtered off and washed with water. The raw product thus obtained in a yield of 90% can be directly oximated without any further purification.

1240 g (4.9 moles) of the thus prepared 2,4-dichlorophenacyl-1H-imidazol is dissolved in 6.2 l methanol. 506.6 g (7.3 moles) hydroxylammonium chloride and 818.2 g KOH (14.6 moles) are added to this solution, which then is heated for one hour under reflux while stirring. After cooling the reaction mixture is poured into 5330 ml aqueous HCl having a concentration of 5% by weight, whereby the oxime product is precipitated. About one hour later the solig product is filtered off and well washed with water. Then after well drying the thus obtained raw product is recrystallized from ethylene glycol monomethyl ether. The pure oxime product, i.e. the (Z)-1-(2,4-dichlorophenyl)-2-(1H-imidazol-1-yl)-ethanone oxime thus is obtained in the form of colourless crystals having a melting point of 227°–229° C. The yield is 89%. The purity and the identity of the obtained product were confirmed by chemical analysis, TLC, NMR and IR absorption spectra.

(b) Preparation of
(Z)-1-(2,4-dichlorophenyl)-2-(imidazol-1-yl)-O-(2,4-dichlorobenzyl)-ethanone oxime nitrate

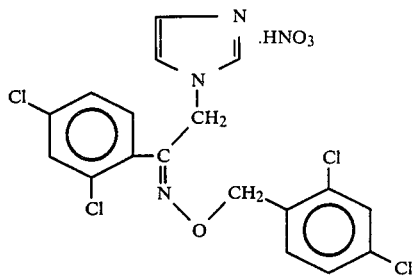

2064 g (7.64 moles) (Z)-1-(2,4-dichlorophenyl)-2-(imidazol-1-yl) ethanone oxime as obtained in the Example is suspended in five times its amount (10.3 l) acetone, vigorously agitated and, as 100% KOH, 386 g KOH (6.88 moles) is added to the suspension in the form of a fine powder of 90% pure KOH. The suspended ethanone oxime is thus gradually dissolved. After about one hour 1554 g (7.9 moles) 2,4-dichlorobenzyl chloride is added to the solution in a single portion. The resulting reaction is slightly exothermic and causes the temperature of the reaction mixture to rise to between 35 and not more than 40° C. In order to complete the reaction the reaction mixture is agitated for 4 additional hours while maintaining the temperature of the reaction at not more than 40° C., with some slight cooling if necessary. Upon completion of the reaction the mixture is poured into 15 l water. Thereafter the product of the reaction is precipitated as the nitrate by adding 6 l of aqueous 2n $HNO_3$.

A few hours after precipitation of the nitrate the mixture is filtered and the precipitate throughly washed with water. The thus separated raw nitrate is recrystallized in 11.3 l of 94% ethanol. A second recrystallization in 3 times the stated amount of ethanol yields the final product in the form of colorless crystals having a purity of 99.95%.

The purity of the obtained product is checked by thermal analysis. The melting point of the resulting crystals is between 139.5° and 140.5° C. The yield of the recrystallized 99.95% pure final product obtained is 62.5%.

Elemental analysis for $C_{28}H_{13}Cl_4N_3O.HNO_3$ (M.W.492.17)

|  | C (%) | H (%) | N (%) | Cl (%) |
| --- | --- | --- | --- | --- |
| Calculated | 43.94 | 2.87 | 11.38 | 28.82 |
| Found | 43.61 | 2.88 | 11.03 | 28.90 |

The NMR spectrum shows δ values of 5.34 and 5.64 ppm for the $CH_2$ proton displacement as contrasted with 5.08 and 5.35 ppm for the other isomer. This finding allows one to identify the obtained product as the (Z)-isomer, as this isomer can be expected to have the greater proton displacements.

COMPARATIVE EXAMPLE

The above example is repeated exactly in the same manner and using the same parameters as described above with the exception that in section (b)—as 100% KOH—463 g KOH (8.26 moles) is added to the suspension of the oxime in the form of a fine powder of the same 90% pure KOH as used in the example.

After recrystallization as described in the above example a product is obtained having a melting point of 132° to 135° C.

The recrystallized product thus obtained is subject to thin layer chromatography. A mixture of 45% dichloromethane, 40% ethylether, 10% formic acid, 5% ethylalcohol and 1% water, all parts by volume, is used as a solvent. The tests were run with effectively 100% pure (Z)-oxime ether as a reference, with the product ether of the above example, and with the recrystallized oxime ether product of the present comparative example. The thus obtained TLC-plate did show dots in one line for all three starting materials, the dot of the material obtained in the comparative example, however, being smaller than the two others and being followed behind by a second dot, when seen from the starting line in the direction of movement. Said following dot is well separated from the leading dot and at least of the intensity as the latter. No such following dot is observed either for the reference or for the product of the above example. By means of a second TLC-run said following dot was identified as the corresponding (E)-oxime ether, so that by means of the above described TLC the ether product obtained in the present comparative example is understood comprising about 50% of the desired (Z)-oxime ether and about the same amount of (E)-oxime ether.

Separation of the two isomers obtained in the comparative example could not be achieved by means of fractional crystallization. The isomer components were finally separated on a chromatographic column.

In brief, running the etherification of the (Z)-oxime in the presence of only a very small super-equimolar amount of the base results via an isomerization process right through to a product consisting of the (E)-oxime ether and the (Z)-oxime ether, both in about equal amounts. For separating both isomeric components no crystallization procedures can be applied, and chromatographic separation is to be used instead. As shown in the example above, such results safely can be avoided when using according to the invention in the etherification step the metal base in an amount slightly less than the equimolar amount based on the starting oxime material.

We claim:

1. A process for preparing substantially pure (Z)-1-(2,4-dichlorophenyl)-2-(imidazol-1-yl)-O-(2,4-dichlorobenzyl)-ethanone oxime ether in its cis-isomer form and having the formula

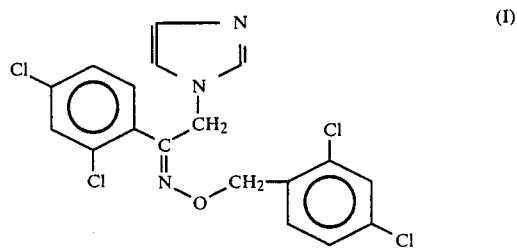

or an acid addition salt thereof with a teleologically acceptable acid; which comprises:
(1) suspending substantially pure (Z)-1-(2,4-dichlorophenyl)-2-(imidazol-1-yl)-ethanone oxime in acetone, (2) adding to the resulting suspension solid KOH in finely subdivided form with vigorous agitation in an amount that is about 5 to 15 mole % less than the equimolar amount of KOH relative to said oxime, and continuing the agitation until the oxime is dissolved, (3) adding to the resulting solution an approximately equimolar amount of 2,4-dichlorobenzyl chloride and thereafter stirring the reaction mixture while maintaining it at a temperature not in excess of 40° C. until substantially complete reaction has been obtained, and (4) pouring the reaction mixture into water or an aqueous solution of a teleologically acceptable acid and recovering the oxime ether product therefrom.

2. A process according to claim 1 wherein aqueous nitric acid is added to the aqueous reaction mixture in step (4), whereby the oxime ether is precipitated as a nitrate salt, and wherein the oxime ether product is recovered in the form of its nitrate.

3. The process of claim 1 wherein the ethanone oxime is suspended in about 5 times its weight of acetone.

* * * * *